United States Patent [19]

Kitchen

[11] Patent Number: 4,900,548

[45] Date of Patent: Feb. 13, 1990

[54] USE OF DIETHYLCARBAMAZINE TO ENHANCE ANTIGEN-ANTIBODY AND ANTIGEN-HOST IMMUNE CELL INTERACTIONS

[75] Inventor: Lynn W. Kitchen, New Orleans, La.

[73] Assignee: Harvard University, Cambridge, Mass.

[21] Appl. No.: 120,561

[22] Filed: Nov. 13, 1987

[51] Int. Cl.[4] ............... A61K 39/02; A61K 45/02; G01N 33/531

[52] U.S. Cl. .................................. 424/88; 514/589; 436/543; 424/85.8

[58] Field of Search ................ 424/85, 86, 87, 88; 514/589; 436/543

[56] References Cited

U.S. PATENT DOCUMENTS

| | | | |
|---|---|---|---|
| 4,710,492 | 12/1987 | Lin et al. | 514/50 |
| 4,724,232 | 2/1988 | Rideout et al. | 514/50 |
| 4,783,446 | 11/1988 | Neushul | 514/54 |
| 4,795,739 | 1/1989 | Lifson et al. | 514/8 |

OTHER PUBLICATIONS

Sharpe et al. "Retroviruses and Mouse Embryos: A Rapid Model for Neurovirulence and Transplacental Antiviral Therapy", Science, vol. 230, 26 Jun., 1987, pp. 1671–1674.

Tavares et al. "3′-Azido-3′-deoxythimidine in Feline Leukemia Virus-Infected Cats: A Model for Therapy and Prophylasis of AIDS", Cancer Research 47, 3190–3194, Jun. 15, 1987.

Hardy et al. "FeLV-Induced Feline Acquired Immune Deficiency Syndrome", Prog. Allergy, vol. 37, pp. 353–376, 1986.

Piessens et al. "Effect of Treatment with Diethylcarbamazine on Immune Responses to Filarial Antigens in Patients Infected with *Brugia Malayi*;"Acta Tropica 38, 227–234 (1981).

Kitchen, "Effect of Diethylcarbamazine on Cats Given Feline Leukaemia Virus Vaccine", Vaccine, vol. 5, Dec., 1987, pp. 266–267.

*Primary Examiner*—John Kight
*Assistant Examiner*—Nathan M. Nutter
*Attorney, Agent, or Firm*—Pennie & Edmonds

[57] ABSTRACT

This invention relates to the use of diethylcarbamazine (DEC), its analogs, homologs, and pharmaceutically acceptable salts thereof as an antiviral agent. This invention further relates to the use of DEC in in vivo diagnosis to increase antibodies to a particular disease; to the use of DEC in in vitro serologic assays to increase efficacy; and to the use of DEC as a vaccine adjuvant.

40 Claims, No Drawings

USE OF DIETHYLCARBAMAZINE TO ENHANCE ANTIGEN-ANTIBODY AND ANTIGEN-HOST IMMUNE CELL INTERACTIONS

1. FIELD OF THE INVENTION

One of the most feared and dangerous diseases of recent times is the syndrome known as acquired immune deficiency syndrome, or AIDS. This disease is caused by a retrovirus, human immunedeficiency virus, or HIV. To date, there is no known cure and no recognized chemoprophylactic which prevents infection. The near epidemic proportions it has reached in certain populations is of course partly due to the present inability to control the virus medically, but also is in part due to the difficulty in identifying infected individuals in the early stages of the disease. It may be several months after initial infection with the virus that an afflicted individual produces sufficient quantities of anti-HIV antibodies to permit detection of the presence of the virus by standard immunodiagnostic techniques. Furthermore, the highest titer of antibodies which are ultimately produced by the infected individual have not at present been found to be sufficient to either destroy the virus or prevent the advancing stages of the disease. Thus, there is currently a need for a means to enhance the immune response of the person with AIDS, and also to improve the present capacity for immunodiagnosis of the disease. Also required are methods which aid in preventing the initial infection and treating an already existing one. The present invention provides a means by which each of the foregoing objectives may be attained.

This invention is in the field of anti-viral/immunomodulator agents and specifically relates to the use of diethylcarbamazine (DEC), its analogs, homologs, and pharmaceutically acceptable salts thereof, as an anti-viral and immunomodulator agent. This invention further relates to the use of DEC in in vivo diagnosis to increase detection of antibodies to specific antigens indicating infection with a particular microorganism or a given neoplasia; to the use of DEC in in vitro serologic assays to increase assay efficacy; and to the use of DEC as a vaccine adjuvant. The methods of the present invention are broadly applicable to a variety of pathogens, but are particularly useful in the treatment and prevention of retroviral infections, and in particular, for HIV and Feline Leukemia viruses.

2. BACKGROUND OF THE INVENTION

2.1. IMMUNE RESPONSE IN VIRAL INFECTIONS

After a virus invades a host cell, it begins to replicate. With DNA viruses, specific virus DNA strands are transcribed into specific messenger RNA (mRNA) which is then translated to synthesize virus-specific proteins and enzymes necessary for biosynthesis of virus DNA. With RNA viruses, single-stranded RNA serves as its own messenger. The mRNA is translated, resulting in the formation of an RNA polymerase. Some of the viral proteins are structural parts of the capsid and others are virus-specific enzymes.

The host responds to the viral invasion in a cascade type of response. Macrophages and polymorphonuclear leukocytes migrate to the area of infection, producing inflammation. Interferons are produced locally, and B, T, and null lymphocytes appear. Macrophages attach to antigen, markedly augmenting the efficacy of virus inactivation by specific neutralizing antibodies or sensitized T lymphocytes. During the first few days of many virus infections there is a circulating lymphopenia of both B and T cells. Lymphocytes migrate to sites of infection and to the liver, spleen, or other organs of the mononuclear phagocytic system.

Proteins of the virus capsid stimulate B lymphocytes (immunoglobulin-bearing, bone marrow-derived) to synthesize humoral antibodies (IgM, IgG, IgA, IgD) and secretory antibodies (IgA). Cell-associated antibodies (IgE) are also produced. Immunoglobulins are synthesized in local lymph nodes, at body surfaces, and in inflammatory exudates within organs. Many molecules of antibody combine with a single virion. Covering a critical number of essential sites on the virion may render an antigen-antibody complex noninfectious.

There are few drugs that exist which effectively combat viruses per se, owing to the difficulty of attacking the virus while leaving uninfected host cells unimpaired. Prevention of some virus infections has instead been achieved primarily through the development of viral vaccines, either live attenuated, and "killed" or inactivated viruses. Passive immunization with pooled human immune serum globulins or globulins with high titers of antibodies to specific agents such as rabies or hepatitis B have also been of some benefit in the prophylaxis of viral infections. These preparations generally are most useful when given early during the incubation period in order to prevent clinical illness.

2.2. HUMAN IMMUNODEFICIENCY VIRUS (HIV)

The Acquired Immunodeficiency Syndrome (AIDS) pandemic has created additional pressing challenges regarding diagnosis, prevention, and treatment of the etiologic agent of AIDS —the human immunodeficiency virus (HIV). HIV has a lipid envelope and is slightly more than 100 nm in diameter. On electron microscopy, HIV has a characteristic dense, cylindrical nucleoid containing core proteins, genomic RNA, and the reverse transcriptase (RT) enzyme that classify HIV as a retrovirus. In addition to the standard gag, pol, and env genes which encode the core proteins, RT and env proteins, respectively, there are 5 additional genes —tat, trs/art, sor, and 3'orf. Protein products of the gag, pol, env, sor, and 3'orf genes are detectable in vitro, and antibodies against these HIV proteins are present in the serum of infected persons (Ho, D. D., et al., *New Engl. J. Med* 317: 278, 1987). Antibodies to the env-encoded gene products, HIV-1 envelope glycoproteins 120 and 160, are the most reliably detected antibodies in serum samples from HIV-1 infected patients (Kitchen, L. W. et al., Nature 312: 367, 1984, and Kitchen, L. W. et al., JID 153: 788, 1986). HIV-1 is the etiologic agent of AIDS and AIDS-related disease in much of the world today. Related retroviruses HIV-2 and HIV-3 result in similar syndromes in West Africa. The spread of AIDS has resulted in unprecedented efforts to identify drugs effective in controlling retroviral infections, in the hope of reducing further transmission of the retroviruses and improving clinical outcome. However, HIV infection is difficult to control —and even more difficult to eradicate —because HIV can remain latent within the infected host, destroy key cells of the immune system resulting in severe immune suppression, and attack the central nervous system —a site relatively protected from immunologic and chemotherapeutic intervention. Azidothymidine (3'-Azido-3'-

Deoxythymidine, also known as AZT, Zidovudine, or Retrovir; Burroughs Wellcome Company) does not eradicate HIV from the infected host, but administration of AZT significantly prolongs survival in some groups of AIDS patients. However, AZT has a relatively short half-life requiring frequent administration and can cause serious adverse effects such as bone marrow suppression requiring blood transfusions (Fischl, M. A. et al., *New Engl. Jour. Med.* 317: 185, 1987; and Richmann, D. D., et al., *New Engl. Jour. Med.* 317: 192, 1987). Other agents, including drugs which stimulate the immune system nonspecifically, are also being tested in HIV-1 infected humans (Lotze, M. T., "Treatment of immunological disorders in AIDS." In: *AIDS-Etiology, Diagnosis, Treatment and Prevention,* DeVita, V. T. et al., (eds.), pp. 235-263, J. B. Lippincott, 1985).

Considerable effort has been recently directed toward developing a vaccine for AIDS, but as of this writing, no HIV-1 vaccine candidates have been successful in preventing HIV-1 infection (III International Conference on AIDS, June 1-5, 1987, Washington, D.C).

That administration of AZT can prevent infection in AIDS animal models such as murine leukemia virus (MuLV) and FeLV (Sharpe, A. H., et al., *Science* 236: 1671, 1987; and Tavares, L., et al., *Cancer Res.,* 47: 3190, 1987) suggests that drug regimens to prevent as well as treat AIDS infection are possible, and that there is an urgent need to develop a simple, effective, and nontoxic drug regimen for persons at high risk worldwide while HIV vaccine efforts continue. Persons at significant risk could include inhabitants in central Africa, wives of hemophiliacs, and health care workers with inadvertent parenteral or mucous membrane exposure to HIV, among others.

It has now been discovered that a known compound diethylcarbamazine (DEC) possesses properties which make it useful in a number of methods associated with the treatment, prevention and diagnosis of viral infections, particularly retroviral infections. Because of its unusual antiviral and immunomodulating properties, it is likely that DEC can play a significant role in the containment of the AIDS epidemic; additional advantages are that it is chemically stable under conditions of heat and humidity, requires less frequent administration than does AZT, and can act as a vaccine adjuvant. Inadvertent ingestion of greater than the recommended amount of drug will generally not induce serious toxicity, and monitoring of blood counts and other parameters in treated patients is not considered necessary. Furthermore, since DEC has been shown to increase antibodies to opportunistic non-retroviruses which frequently accompany retroviral infection, DEC administration may simultaneously mitigate retroviral and non-retroviral opportunistic infections in HIV-infected hosts. Additionally, DEC is useful as treatment or adjunct treatment with antibiotics, other chemotherapeutic agents, monoclonal or polyclonal antibodies and/or vaccines, in virtually any infectious or neoplastic disease in retroviral or non-retroviral infected hosts, both animal and human, by improving the host's immune response to key infectious or neoplastic antigens, and by removing infectious agents and neoplastic cells from the circulation.

The AIDS pandemic has also created a need for increasingly widespread testing of humans for evidence of HIV infection. DEC increases absorbance values generated by serum samples from AIDS patients when tested by commercial enzyme immunoassay for antibody to HIV-1. DEC increases detection of antibody to feline oncornavirus-associated cell membrane antigen (FOCMA) by indirect membrane immunofluorescence (IMI) in feline leukemia virus (FeLV) infected cats. DEC is thus useful in improving antibody and antigen assays.

3. SUMMARY OF THE INVENTION

This invention relates to the use of diethylcarbamazine (DEC), its therapeutically useful analogs, homologs, and pharmaceutically acceptable salts thereof as an anti-viral/immunomodulator agent, and compositions containing same. This invention further provides a method of use of DEC in in vivo diagnosis, to increase antibodies to a particular disease; and to a method for the use of DEC in in vitro serological and antigen assays to increase efficacy. Finally, DEC has proven useful as an adjunct or adjuvant, in combination with other antiviral compounds or compositions. The present methods and compositions are applicable to treatment and detection of both viral and non-viral pathogens.

4. DETAILED DESCRIPTION OF THE INVENTION

4.1. ANTIFILARIAL PROPERTIES

It has now been found that diethylcarbamazine (N,N-diethyl-4-methyl-1-piperazine carboxamide; DEC) is useful in the treatment of viral infections, particularly retroviral infections. It has also been found that DEC may be used additionally in in vitro serological assays to increase assay efficacy; in in vivo diagnosis to increase detection of antibodies to specific antigens of infectious agents or neoplasms; and also as a vaccine adjuvant.

Although not wishing to be bound by a single mechanism of action, it is the inventor's hypothesis that the antiviral/immunomodulator actions of DEC may be due to increased specific host immune responses following enhancement of antigen-antibody interactions (resulting in clearance of circulating virus) and antigen-host immune cell interactions. The stating of this hypothesis is not meant to preclude the formation of other hypotheses concerning other modes of action of DEC.

DEC is currently the mainstay of prevention and therapy of the filariases. Injection of DEC in filarial-infected cotton rats has resulted in an extremely rapid decline (80% decrease in 1 minute) in the number of circulating microfilariae, resulting in destruction of microfilariae by macrophages within the hepatic system, but not by macrophages in the peripheral blood (Hawking, et al., *Br. J. Pharm.* 5: 217, 1950). DEC promoted adherence to peripheral blood leukocytes of microfilariae in vitro in the presence of human serum containing high titers of IgG antibodies to microfilarial sheaths. DEC did not decrease circulating microfilariae in experimental animals unless antibodies to microfilarial sheaths were also present (Piessens, et al., *Nature* 282: 845, 1979). One possible onclusion from these reports is that DEC alters the microfilarial surface, rendering microfilariae more susceptible to interaction with antibodies and host cells.

Although neither DEC nor serum from microfilarial-infected subjects treated with DEC shortened the survival of microfilariae in vitro (Hawking, et al., *Br. J. Pharm.* 5: 17, 1950), later studies indicated that DEC-induced, platelet-derived free radicals could kill microfilariae in an *in vitro* system (Cesbron, J. et al., *Na-* ture 325: 533, 1987). This action of DEC appears distinct from the drug's other immunomodulatory properties, although DEC-induced killing of microfilariae by this mechanism may further augment DEC-induced anti-microfilarial immune responses.

DEC has been shown to increase both specific humoral and cellular immune responses to filarial infection. In one study, serum titers of antibody to microfilarial sheaths increased in 3 of 7 patients who had become amicrofilaremic after DEC treatment. In vitro lymphocyte proliferative responses to microfilarial antigens (but not microfilarial-unrelated antigens) increased in patients who became amicrofilaremic after treatment with DEC (Piessens et al., *Acta Tropica* 38: 227, 1981).

4.2. ANTIVIRAL PROPERTIES

It has now been unexpectedly discoverd that DEC has antiviral properties, and is particularly effective against retroviral infection. DEC is an orally bioavailable drug that penetrates well into all body tissues and fluids except fat. The toxicity of DEC is low generally, with nausea and vomiting reported with oral doses in humans exceeding 10 mg/kg/day as a single dose per day. The only reported toxicity associated with DEC treatment has occurred in certain nematode-infected hosts, in whom untoward host immune responses, such as anaphylaxis, have sometimes followed rapid death of the worms (Warren, K. S., et al., eds. *Tropical and Geographic Medicine*, N.Y., McGraw-Hill, 1984), but does not represent a direct toxic effect of DEC itself. For decades, domestic dogs (including pregnant bitches) have been given DEC daily during the growing season as prophylaxis for heartworm infection, without apparent teratogenic or other untoward effects in the pups. Similarly, no adverse effects of human fetuses has been noted. Despite the evidence that DEC increases antigen-antibody interactions, DEC has never been noted to induce immune complex diseases such as immune-complex glomerulonephritis, a kidney disorder.

The structural formula of DEC is as follows:

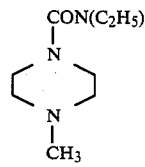

Both the in vitro and in vivo effects of DEC have been demonstrated with the present invention. In the in vivo testing of DEC, it was surprisingly discovered that DEC adminstration had an array of positive effects on the recipient's immune response to retroviral infection. The observable effects include an increase in detectable antibody titer to infectious virus, a decrease in detectable serum infectious virus, and also an increasing titer of antibodies following anti-viral vaccine administration when DEC is added as a vaccine adjuvant. These observations are more than just interesting artifacts, however; there is also a substantially increased survival rate among retrovirus infected hosts that have been treated by DEC administration, when compared with untreated controls. An additional added benefit is the apparently broad range of pathogens to which the method is applicable: DEC has been also shown to increase antibody titers to opportunistic pathogens which frequently accompany retroviral infection. These aforementioned in vivo effects have been specifically demonstrated with Feline Leukemia Virus (FeLV), a recognized animal model for AIDS, and an associated opportunistic infection, Feline Infectious Peritonitis, caused by a coronavirus.

As for in vitro application, the addition of DEC to a standard immunoassay has been shown to substantially increase the efficacy of such assays to detect antibodies in serum. The increased efficacy results in improved positive predictive value without any sacrifice of test sensitivity.

Thus, according to the methods of this invention, DEC may be used in a variety of ways:

(1) as an anti-viral agent;

(2) as an immunomodulator, i.e., to increase detectable titers of antibodies to retroviral and non-retroviral pathogens which may mitigate a variety of infections and neoplasias in both immunocompromised and non-immunocompromised hosts;

(3) as a vaccine adjuvant;

(4) in in vivo diagnosis to increase antibodies to key infectious or neoplastic antigens;

(5) in in vitro serological assays to increase efficacy. Each of the above utilities is more clearly elucidated in the examples to follow.

As used herein DEC is meant to include diethylcarbamazine and therapeutically active homologs and analogs thereof. It is also meant to include pharmaceutically acceptable salts of DEC, such diethylcarbamazine citrate or dicitrate, or other acid-addition salts.

4.3. APPLICATION AND ADMINISTRATION

In its previously known therapeutic application, i.e., in microfilarial treatment, DEC has been routinely administered orally, but also has been given by the intraperitoneal and transdermal route. For purposes of the present invention, both oral and parenteral administration, also including intravenous, subcutaneous, and intramuscular administration, are contemplated. DEC penetrates well into all animal body tissues and fluids, except fat, after oral administration.

4.3.1. THERAPEUTIC AND PROPHYLACTIC USES

The activity of DEC in treatment of viral infection is clearly demonstrated with more than one type of virus, and the present method contemplates the treatment of all types of viruses. The method of treatment has been shown to be particularly effective in control of coronavirus and retrovirus. The preferred application of the present therapeutic method is in connection with retroviral infection, the retroviruses including HIV-1, 2, and -3, feline leukemia virus, feline sarcoma virus, Rous sarcoma Virus, and avian leukosis viruses, among other well known oncoviruses. Of greatest interest is the treatment of the AIDS, and AIDS-related diseases, and feline leukemia virus. Because of the now-established effectiveness for very different types of pathogens (i.e., microfilarial worms and viruses), it is also expected that the present methods are applicable to bacterial and protozoan pathogens as well. A therapeutic regimen for the treatment of an already established infection will typically require administration of about 0.5–20 mg per kilogram of body weight, the exact dose depending upon mode of administration. The preferred dosage is about 10 mg/kg/day, for one month, as a single oral dose, with proportionately smaller amounts normally being used for parenteral administration. Similar dosages are employed when the active agent is used as an immunomodulator. For prophylactic administration, dosages will be typically 0.5–20 mg/kg administered 1–7 times per week.

DEC is, as noted, also useful as an adjuvant both with traditional vaccine preparations and also with chemotherapeutic agents used in treatment of infection. Administration of the adjuvant may take place simultaneously with the primary therapeutic or prophylactic agent, and also may be administered subsequently to the primary administration. For this purpose, the mode of administration of DEC will typically be in accordance with that of the primary agent, but in any event may be either oral or parenteral. A suggested program would be administration of about 10 mg/kg/day orally as a single dose for at least two weeks following vaccination, or alternately, about 0.5 ml (containing about 0.05–2 mg DEC/ml) added to the vaccine preparation to be administered parenterally. Among the types of HIV vaccine preparations with which use of DEC is contemplated are subunit vaccines containing HIV antigens, including HIV envelope glycoproteins (gp120 and gp160), the HIV transmembrane glycoprotein (gp41) and HIV gag encoded protein (p24), killed whole virion HIV vaccines, or Vaccinia virus vectors containing HIV antigens. Also useful are combinations of DEC with anti-viral chemotherapeutic agents such as AZT, fusidic acid, Ampligen, interferon, interleukin-2, IMREG-1, and dideoxycytidine (DDC). Possible variation of the aforementioned regimens, with respect to dosage, mode of administration and possible combinations will be readily apparent to one skilled in the art, and may be achieved without undue experimentation.

4.3.2. IN VITRO APPLICATIONS

In vitro utility of DEC may be at least partially related to in vivo administration of the drug; in other words, the administration of DEC to a patient to be tested for presence or absence of antibodies diagnostic for a particular pathogen prior to serum testing will significantly increase antibody titer and thus, effectively render the subsequent assay more sensitive. Doses comparable to that given for therapy or prophylaxis of retroviral infection should be given daily from 1–30 days, and serum antibodies measured from 7–30 days after initial DEC administration. However, in vitro utility is also achieved by addition of small amounts of DEC to the serum sample to be tested in a diagnostic immunoassay; the addition of DEC apparently, in some unknown manner, enhances the antigen-antibody reaction upon which the success of the immunoassay depends. The amount of DEC used for any particular immunoassay depends to some extent upon the antigen used for antibody binding; however, determination of an optimum amount is relatively easy to ascertain by routine manipulation using positive and negative standards. Although DEC has been shown to increase antigen antibody bindings in concentrations as low as 0.002 mg/ml, the amount of DEC usually added. Usually, the amount of DEC added to the serum diluent will be approximately 5 mg/ml, pH adjusted to about 7.3–7.4 with NaOH (4N). Passage of the serum sample through a 0.45 micron filter, for removal of any debris, is preferably performed before analysis.

Because of the apparent generality of the enhancement of antigen-antibody interaction, this method can be employed with virtually any type of immunoassay in which an antibody-antigen reaction is used as the indicator of the existance of a particular condition in a fluid sample. The types of assays contemplated for use may be either qualitative or quantitative, and include both single site or two-site (sandwich) assays of the non-competitive type, as well as traditional competitive binding assays. These assays typically employ a reporter molecule for visual identification of the occurrence of an antigen-antibody reaction, such as an enzyme, a radioisotope, a fluorophore or a chemi- or bioluminescent molecule; the present method may be employed in any of these variations. The use of DEC in improving immunoassay sensitivity and accuracy is not limited to detection of a particular type of antibody, but may be applied to an immunoassay for any type of antigen or antibody, by addition of DEC to the fluid sample to be tested. A preferred application, however, is the detection of anti-retroviral antibodies, in particular anti-HIV antibodies.

The various aspects of the invention are further described by the following examples. These examples are not intended to limit the invention in any manner.

5. EXAMPLE

5.1. ADDITIONAL BACKGROUND INFORMATION FOR EXAMPLES I-VI

Infection of cats by feline leukemia viruses (FeLV), a family of T-lymphotropic retroviruses, may result in immunosuppression. Specifically, lymphopenia, depressed cell-mediated immune response, thymic atrophy, and decreased humoral response to T cell-dependent novel antigens despite hypergammaglobulinemia have been documented in FeLV-infected cats. Such cats frequently die of opportunistic infections or neoplasias. (Essex, et al. *Infect. Immunity* 11: 470, 1975; Perryman, et al., *J. Nat. Can. Inst.* 49: 1357, 1972; Hoover, et al., *Cancer Res.* 33: 145, 1973; Wernicke, et al., *J. Virol.* 60: 669, 1986; Trainin, et al., *Science* 220: 858, 1983.

FeLV-infected domestic cats were chosen for the experiments described in Examples I, II, III, IV, V, and VI, since this retroviral-host model has been studied extensively. Chronic FeLV infection in cats ——like HIV-1 infection in humans ——causes immunosuppression and high mortality. The concentration of infectious virions in the serum samples in a significant proportion of chronically infected FeLV cats is high, and can be quantitated using the 81 cell focus induction assay of Fischinger (Fischinger, et al., *J. Virol.* 14: 177, 1974). The role of serum antibodies to FeLV has been investigated. Significant titers of serum neutralizing antibodies to FeLV and antibodies to feline oncornavirus-associated cell membrane antigen (FOCMA), have been associated with resistance to FeLV viremia and FeLV-related neoplasia respectively (Essex, et al., *Nature* 233: 195, 1971; Essex, et al. *Science* 190: 790, 1975; Hardy, et al., *Cancer Res.* 36: 582, 1976). The presence of FeLV antigens in peripheral blood leukocytes (Hardy, W. D., Jr., et al., *Nature* 244: 266, 1973) is commonly used to diagnose FeLV infection in cats. However, FeLV-infected cats continued to test positive for FeLV leukocyte antigens after treatment with the anti-retroviral agent suramin despite a reduction in serum viral infectivity using the 81 cell focus induction assay (Cogan, D. C., et al., *Am. J. Vet Res* 47: 2230, 1986).

EXAMPLE I: EFFECT OF DEC ON SERUM ANTIBODY TO FOCMA IN FELV CATS

MATERIALS AND METHODS

Cats: A total of 39 cats were studied. Of these 39, 33 had known exposure to FeLV, including 27 testing positive for FeLV leukocyte antigen. DEC treatment was given to 22 cats testing positive for FeLV leukocyte antigen and 6 cats with known exposure to FeLV that tested negative for FeLV leukocyte antigen. In addition, DEC treatment was given to 2 specific pathogen-free (SPF)/FeLV-naive cats to exclude false-positive antibodies. Five FeLV leukocyte antigen positive and 4 SFP/FeLV-naive cats were used as untreated controls.

Drug: Treated cats were given 10 mg/kg/day DEC orally as a single dose per day for one month.

FOCMA antibody and FeLV leukocyte antigen testing: Blood samples for antibody to FOCMA and FeLV leukocyte antigen were drawn the day prior to initiating DEC treatment and within one week following the end of treatment. Untreated cats were also evaluated for these 2 parameters before and after one month observation. Serum samples were analyzed for antibody to FOCMA by indirect membrane immunofluorescence on FL-74 cells as described previously (Essex, et al., *Int. J. Cancer* 8: 384, 1971), using 10-fold dilutions (1:10$^1$ to 1:10$^5$) of serum diluted with phosphate-buffered saline after exhaustive absorption of the serum samples with freshly isolated normal feline lymphocytes. Antibody titers were reported as the highest serum dilution in which >50% of the observed FL-74 cells fluoresced. FeLV viral antigen in peripheral blood leukocytes was tested at the Laboratory of Veterinary Oncology, Memorial Sloan-Kettering Cancer Center, New York City, as described previously (Hardy, W. D., Jr., et al., *Nature* 244: 266, 1973).

RESULTS

Antibody to FOCMA was undetectable (at 1:10 dilution of serum) in 9 FeLV leukocyte antigen positive cats before DEC treatment. All 9 cats testing positive (>1:10; geometric mean titer or GMT =278) for antibody to FOCMA after DEC treatment. Higher post-treatment titers of antibody to FOCMA were noted in 13 of 13 FeLV leukocyte antigen positive cats and 4 of 6 FeLV-exposed/FeLV leukocyte antigen negative cats that initially tested positive for this antibody (pretreatment GMT of 19 cats =264; posttreatment GMT =6,158). The 5 untreated FeLV leukocyte antigen positive cats tested negative for antibody to FOCMA before and after 1 month observation. The 4 FeLV-naive untreated cats and the 2 DEC-treated FeLV-naive cats also tested negative before and after one month observation (see Table 1).

EXAMPLE II: EFFECT OF DEC ON SERUM VIRAL INFECTIVITY IN FELV CATS

MATERIALS AND METHODS

Cats: Fourteen (14) outbred cats testing positive for FeLV antigen in peripheral blood leukocytes that had serum samples containing high titers of infectious virus by the assay of Fischinger (mean: 1.39 × 10$^5$ focus forming units or FFU/ml serum; Fischinger, P. J. et al., *J. Virol.*, 14: 177, 1974). Cats were tested for FeLV leukocyte antigen and serum infectious virus before and after one month treatment with DEC.

Drug: Treated cats were given 10 mg/kg/day DEC orally as a single dose per day for 1 month.

FeLV leukocyte antigen testing: as per EXAMPLE I, above.

RESULTS

Serum viral infectivity became undetectable one month after initiating treatment in 12 cats, after 90 days in 1 cat, and after 300 days in 1 cat. Three untreated naturally-infected positive control cats continued to have high titers of serum infectious virus. Both treated and untreated cats continued to test positive for FeLV antigen.

EXAMPLE III: EFFECT OF DEC ON VERTICAL TRANSMISSION ON FELV

One naturally-infected cat was donated by the owner to the Harvard School of Public Health when the cat was approximately 1 month pregnant and treated during the last four weeks of her pregnancy. Her four kittens tested negative for FeLV leukocyte antigens at 10 days of age but tested positive at age 2 months.

This is the first report of a FeLV leukocyte antigen positive queen that delivered FeLV kittens testing negative during the first 2 weeks of life for FeLV leukocyte antigens (Hoover, E. A., et al., *Leukemia Rev. Intl.* 1: 7, 1983). Thus it is likely that DEC treatment decreased the amount of maternal FeLV to which the kittens were exposed, or delayed transmission by other means. It is also possible that vertical transmission may have occurred prior to DEC treatment of the queen. Latent FeLV infection could then have been reactivated in the kittens after weaning, when levels of maternal antibody waned (Hoover, E. A., et al., *Infect. Immunity* 16: 54, 1977).

EXAMPLE IV: EFFECT OF DEC ON SURVIVAL IN FELV-INFECTED CATS

PROSPECTIVE TRIALS

METHODS

Cats: Eight cats ——2 sets of 4 littermates each ——were studied in 2 open prospective controlled trials. One set of 4 littermates (Group A) had been inoculated with the Rickard strain of FeLV at about 6 weeks of age. Two cats of this litter were treated with DEC 10 mg/kg/day orally as a single dose per day for 1 month ——approximately 9 months post-inoculation. Another group of 4 littermates (Group B) were offspring of an FeLV queen. Two cats of the litter were treated with DEC 10 mg/kg/day as a single oral dose per day continuously beginning at age 2 months ——when the kittens first tested positive for FeLV leukocyte antigens. The 1 remaining treated cat is still alive.

RESULTS

Average survival among treated cats in Group A was prolonged three months in comparison with untreated cats. Average survival among treated cats in Group B was prolonged 2.5 months in comparison with untreated cats.

HISTORICALLY CONTROLLED TRIALS

The mortality rate among 20 naturally-infected, privately-owned adult cats were treated with DEC 10 mg/kg/day for 1 month. The mortality rate among these 20 cats, is 11 deaths per 513 cat-months follow-up, or 2.14 deaths per 100 cat-months of follow-up.

This result represents improved survival compared to a historical trial involving 134 untreated FeLV cats (mortality 3.46 deaths per 100 cat-months; Francis, D. P. et al., *Am. J. Epid.*, 111: 337, 1980.

Two of the 22 DEC-treated FeLV-infected cats treated with DEC had previously been treated with multiple injections of monoclonal antibodies to FeLV proteins (Cotter, S. M., et al. *Proc. Am. Coll. Vet. Int. Med.*, 13:[3-13]6, 1986) and both cats are still alive (0 deaths/104 cat-months follow-up to date).

EXAMPLE V: EFFECT OF DEC ON ANTIBODY TO FOCMA IN CATS GIVEN FELV VACCINE

ADDITIONAL BACKGROUND

LEUKOCELL, a currently available retroviral vaccine, is given to prevent FeLV infection in cats. LEUKOCELL has been reported to induce FeLV antibodies and prevent infection with FeLV as determined by subsequent viral challenge. However, studies suggest that mechanisms other than virus neutralizing antibodies may be partly responsible for the protective effects offered by LEUKOCELL and other FeLV vaccines (Pederson, N. C. et al., *Feline Practice* 15: 7, 1985, and Osterhaus, A., et al., *J. Immunol.* 135: 591, 1985).

METHODS

The effect of serum antibody to FOCMA and white blood cell counts was investigated in a 2-week course of therapy with DEC (10 mg/kg/day orally) as a single dose begun the day of a single i.m. dose of LEUKOCELL in 2 FeLV-naive cats, and 1 cat with previous household exposure to FeLV. Two FeLV-naive cats and 1 FeLV-exposed cat were given the same dose of LEUKOCELL without DEC. The pre-vaccine serum antibody to FOCMA titer of the 2 FeLV-exposed cats was 1:10. These 2 cats had previously received DEC for a short period for other indications. All 6 cats used in this study were adults. The FeLV-naive cats were obtained from specific pathogen-free breeding colonies and all cats were housed at the Harvard School of Public Health. Blood samples were obtained prior to vaccination and at the end of 2, 6, and 10 weeks after vaccination. All cats were tested for the presence of FeLV antigens in peripheral blood leukocytes prior to and after vaccination by the Laboratory of Veterinary Oncology Sloan Kettering Memorial Cancer Center, New York City. Tests for antibodies to FOCMA were performed as described in EXAMPLE I. Serum alanine aminotransferase and creatinine determinations were obtained 2 weeks after vaccination.

RESULTS

Some of the results are displayed in Table 2. All cats tested negative for the presence of FeLV antigens in peripheral blood leukocytes before and after the experiment. All 4 FeLV-naive cats tested negative for serum antibody to FOCMA before treatment. All vaccinated cats tested positive for serum antibodies to FOCMA 6 weeks after vaccination. However, the mean titer was higher in cats also treated with DEC. Of the previously FeLV-naive cats, only those which were vaccinated/treated tested positive for antibody to FOCMA 10 weeks after vaccination. The average monocyte count increased from 27 to 272 (10-fold increase) in the vaccinated/treated group 2 weeks post vaccination, and from 87 to 127 in the vaccinated/untreated group (1.3-fold increase). No other significant changes in blood counts or serum chemistries were noted.

Since macrophages are derived from monocytes and process novel antigens and thus are key cells for both humoral and cellular immune function in humans, the described increase in monocyte counts signal increased immunity to vaccine antigen(s). These findings indicate that DEC treatment given with a single dose of LEUKOCELL increases both the titer and duration of serum antibody to FOCMA. DEC is a relatively nontoxic, readily available and inexpensive drug. Further investigations using the above preliminary findings may optimize development and effectiveness of retroviral and other vaccines.

EXAMPLE VI: EFFECT OF DEC ON ANTIBODY TO FELINE INFECTIOUS VIRUS IN CATS

ADDITIONAL BACKGROUND

The effect of DEC treatment on serum antibodies to feline infectious peritonitis (FIP) was examined. FIP, caused by a cornonavirus, is a common and often fatal opportunistic infection of FeLV-infected cats. Approximately 50% of clinically evident FIP infections occur in FeLV-infected cats (Hardy, W. D., Jr., *Feline Leukemia Virus Diseases*. In: Proceedings of the Third International Feline Leukemia Virus Meeting (Eds. Hardy, W. D., Jr. et al., Elsevier/North-Holland, New York, pp 3-31, 1980). The effect of DEC treatment on serum antibodies to toxoplasmosis, which rarely causes clinical disease in FeLV cats, was also investigated.

METHODS

Fourteen cats were studied; 7 of these 14 were treated with DEC and 7 were untreated. Each group of 7 consisted of 3 FeLV leukocyte antigen negative cats given 1 cc LEUKOCELL FeLV vaccine i.m. (Norden Laboratories, Lincoln, NE) and 4 FeLV-infected cats. All 4 FeLV-infected cats gave positive results for FeLV antigens in peripheral blood leukocytes (determined as per EXAMPLE I). All 14 cats were tested for FeLV leukocyte antigens twice, at 0 and 8 weeks, when serum samples were drawn for FIP antibody titers. Details regarding the mode of infection of the FeLV-infected cats are given in Table 3. DEC was given orally at 10 mg/kg/day as a single daily dose for courses ranging from 2 weeks to continuous treatment, as stated in Table 3. All 14 cats were housed at the Harvard School of Public Health. Serum samples were drawn before DEC treatment and 8 weeks later. Titers of serum antibody to feline infectious peritonitis and toxoplasmosis were determined under code via indirect membrane immunofluorescence (IMI) on infected acetone-fixed target cells by Tufts Diagnostic Veterinary Laboratory, Jamaica Plain, MA. The ATCC VR-867 Dahlberg strain of FIP and the RH strain of toxoplasmosis were used for these studies. All 14 cats remained healthy throughout the study period.

RESULTS

In the DEC-untreated group, the serum antibody titer to FIP increased 4-fold in 2 FeLV-infected cats. In the treated group, 3 cats showed significant rises in serum antibody titers of FIP. Such titers increased 4-fold in 2 treated cats. Of these, 1 cat was FeLV-vaccinated/previously FeLV-naive. Serum antibodies to FIP increased 16-fold (repeated to ensure accuracy) in an additional DEC-treated FeLV-infected cat. Furthermore, some increase in serum antibody titers to FIP were noted in both DEC-treated, FeLV-vaccinated cats that were previously FeLV-naive, whereas no titer increases were observed in the DEC-untreated vaccinated controls (see Table 3). Thirteen of the 14 observed cats gave negative results (>1:16 titer) for serum antibody to toxoplasmosis. The 1 cat giving positive results (1:64 titer) for toxoplasmosis antibody was treated with DEC; the titer did not change after treatment. These data may reflect lack of evidence for active toxoplasmosis infection in the 14 cats.

Adequate titers of serum antibody to FIP have not been proved to protect cats from FIP infection or FIP-related disease. However, an untreated offspring of an FeLV-infected queen (see footnote d in Table 3) was euthanatized approximately 12 months after first testing positive for FeLV leukocyte antigens because of fever, vomiting, and diarrhea unresponsive to antibiotics and supportive care. Findings at necropsy were consistent with feline infectious peritonitis. This is the only cat of the 14 study animals that has developed evidence of FIP disease. The data presented in this report suggest that DEC treatment results in higher titers of serum antibodies to non-retroviral infectious agents such as FIP, in addition to retroviral agents such as FeLV.

EXAMPLE VII: EFFECT OF DEC IN VITRO ON TESTING FOR FOCMA ANTIBODY IN SERUM SAMPLES FROM FELV CATS

METHODS

Serum samples from 10 cats were analyzed for antibody FOCMA as described in EXAMPLE I. Five of the cats tested positive for FeLV leukocyte antigens as described in EXAMPLE I, and all 5 had high titers of serum infectious virus by the assay of Fischinger (see EXAMPLE II). The remaining 5 cats were from specific pathogen-free breeding colonies and known to be FeLV-naive; all 5 tested negative for FeLV leukocyte antigens and serum infectious virus.

RESULTS

In vitro addition of DEC to the serum diluent (5mg/ml; pH adjusted to 7.3-7.4 with 4N NaOH; followed by filtration through a 0.45 micron filter to remove any debris) resulted in detection of antibody to FOCMA ($1:10^1$ dilution) in 5 of 5 serum samples from FeLV-infected cats, whereas all 5 samples tested negative (<1:10 dilution) without DEC. Antibody to FOCMA was not detected in serum samples from FeLV-naive cats, with or without addition of DEC to the serum diluent.

EXAMPLE VIII: EFFECT OF DIETHYLCARBAMAZINE IN VITRO ON TESTING HUMAN SERUM SAMPLES FOR ANTIBODY TO HIV-1

METHODS

Of 140 human serum samples tested for antibody to HIV by commercial enzyme immunoassay (EIA), 75 were form asymptomatic persons testing negative for HIV antibody by radioimmunoprecipitation and sodium dodecyl sulfate polyacrylamide gel electrophoresis (RIP-SDS/PAGE), including 20 blood bank donors, 30 dialysis patients, 15 hemophiliacs, and 10 wives of seronegative hemophiliacs. The remaining 65 samples tested positive for HIV-1 antibody (RIP-SDS/PAGE), and included samples from 57 hemophiliacs, 2 wives of sereopositive hemophiliacs, and 6 non-hemophiliac patients. OF these 65, 40 were form asymptomatic persons and 25 from patients with AIDS-related disease. Seven additional serum samples from AIDS patients were tested by western blot for HIV antibody profiles.

Serum samples from 140 persons were tested for antibody to HIV both by RIP-SDS/PAGE using H9/HIV-1-(HTLV-III)-infected cells and by the ABBOTT antibody to HIV-1(HTLV-III) EIA. Absorbance values were determined with a Quantum II Analyzer (ABBOTT Laboratories, North Chicago, IL). RIP-SDS/PAGE analysis was performed at the Harvard School of Public Health as described previously (Kitchen, L. W., et al., Nature 312: 367, 1984).

T-cell subsets ere performed on blood lymphocyte samples using monoclonal antibodies to Leu-3 (helper-/inducer T cells), Leu-2 (suppressor/cytotoxic T cells), and Leu-4 (total T cells).

RESULTS

The addition of DEC to the serum diluent did not alter the HIV-1 serologic profiles or background of the serum samples from the 7 AIDS patients tested by western blot. However, the gp160 bands yielded by 4 of the 7 samples were slightly more intense with the addition of DEC.

Some of the results regarding the addition of DEC to the serum diluent during testing of antibody to HIV by EIA appear in Tables 4, 5, and 6. Samples from 65 persons testing positive for antibody to HIV by RIP-SDS/PAGE all tested positive by EIA with or without addition of DEC. Of these 65 samples, 22 (15 from asymptomatic persons and 7 from patients with AIDS-related disease) yielded absorbance values >2 (the upper limit of positivity recorded by the Quantum II Analyzer) with and without addition of DEC to the serum diluent, and were omitted from these statistical analyses.

The remaining 43 samples consisted or 25 samples from asymptomatic persons and 18 samples from patients with AIDS-related diseases. The "DEC difference" for a given sample is the number obtained by subtracting the absorbance value yielded by a sample without DEC from the absorbance value generated by the same sample with DEC. The DEC differences were positive for 12 of the 25 asymptomatic cases, and negative for the remainder. The null hypothesis, that the median of the distribution of the DEC differences =0, was tested against the alternative hypothesis that the median was >0 by means of a 1-tailed sign test (using the normal approximation with continuity correction and level of significance 0.05). The null hypothesis was not rejected. The DEC differences were positive for 16 of the 18AIDS-related patients, and negative for the remainder; the corresponding sign test for this group (using the binomial distribution) rejected the null hypothesis ($p<.0007$).

These 43 serum samples included 25 patients who tested positive for antibody to HIV-1 env glycoproteins but negative for antibody to gag gene-encoded p24 by RIP-SDS/PAGE. The DEC differences were positive for 18 of the 25 patients, and negative for the remainder; the corresponding sign test for this group rejected the null hypothesis ($p<.03$). The DEC differences were positive for 6 of the 18 remaining samples that tested positive for both antibody to HIV-1 gag and env proteins; the null hypothesis was not rejected.

Also included among these 43 serum samples were 14 samples from patients <500 helper/inducer T-lymphocytes/mm³ blood. The DEC differences were positive for 11 of the 14 samples; the corresponding sign test for this group (using the binomial distribution) rejected the null hypothesis (p<0.03). The remaining 29 patients had >500 helper T-lymphocytes/mm³ blood; the DEC differences were positive for 13 of the 29 samples and negative for the remainder; the null hypothesis was not rejected.

Among 75 persons testing negative for antibody to HIV by RIP-SDS/PAGE, 17 tested positive by EIA without DEC and 15 tested positive with DEC. The DEC differences were positive for 37 of the 75 and negative for the remainder; a 1-tailed sign test of the null hypothesis that the median was =0 did not reject the null hypothesis at the 0.05 level of significance.

CONCLUSIONS

DEC may more consistently enhance detection of antibody to FOCMA in serum samples from FeLV cats because FOCMA antigens are not known to be present in serum samples of FeLV cats, although FOCMA may be present in nascent (but not mature) FeLV virions associated with FeLV C-infected cells (Vedbrat, et al. *Virology* 124: 445, 1983). DEC may less dramatically/consistently improve detection of antibodies to HIV because such patients' serum samples may also contain HIV antigens or HIV virions, and DEC may enhance binding of HIV antigens used in commercial assays. However, DEC in vitro increases absorbance values generated by HIV antibody testing of serum samples from (1) patients with AIDS-related disease; (2) patients who test positive for env gene-encoded glycoproteins (gp120 and gp160) but not gag gene-encoded proteins (p24 and p55) of HIV-1; and (3) patients with <500 T-helper lymphocytes/mm³ blood. These 3 groups consist of significantly immunocompromised HIV-1 infected patients (Kitchen, L. W., et al., JID 153: 788, 1986). One possible explanation for the above findings is that the rate of in vivo HIV-1 genetic changes ——approximately $10^{-2}$ to $10^{-3}$ nucleotide substitutions per site per year for env and 10-fold fewer for gag may prevent HIV-infected immunocompromised patients from mounting an optimal serologic response in later stages of HIV infection (Hahn B. H. et al., *Science* 232: 1548, 1986). Such patients' serum samples could contain antibodies that do not bind to circulating variant HIV glycoprotein antigens, but could bind to less variant HIV glycoproteins used in commercial kits, and DEC could enhance the latter process. This hypothesis could also explain why the addition of DEC in vitro resulted in slightly more intense HIV-1 gp160 bands generated by samples from 4 of 7 AIDS patients.

The use of DEC in vitro to optimize detection of antibody to HIV-1 glycoproteins may be important to the successful differential diagnosis of patients with AIDS or AIDS-related diseases ——or HIV-1 infected, immunocompromised patients ——since such patients may have low amounts of antibody to gp120 and gp160, and even lower or undetectable amounts of antibody to p24 or p55.

Since in vivo DEC treatment alters titers of serum antibody to non-retroviruses such as FIP (see EXAMPLE VI), these results also may have implications for strategies to improve assays for some antibodies to non-retroviral infectious agents or related antigens.

Having now fully described this invention, it will be appreciated by those skilled in the art that the same can be performed within a wide range of equivalent parameters of concentrations, conditions, and methods, without departing from the spirit or the scope of the invention or any embodiment thereof.

TABLE 1

Effect of Diethylcarbamazine treatment on antibodies to FOCMA in FeLV cats

| Cat group | No. cats in group | No. FeLV leukocyte antigen pos. cats in group | Antibody to FOCMA before/after 1 month DEC treatment | | |
|---|---|---|---|---|---|
| | | | Titers before | Titers after | No. cats |
| DEC-treated/FeLV-exposed | 22 | 22 | <$10^1$ | $10^1$ | 4 |
| | | | <$10^1$ | $10^2$ | 1 |
| | | | <$10^1$ | $10^4$ | 4 |
| | | | $10^1$ | $10^4$ | 2 |
| | | | $10^2$ | $10^4$ | 2 |
| | | | $10^3$ | $10^4$ | 9 |
| Untreated/FeLV-exposed | 5 | 5 | <$10^1$ | <$10^1$ | 5 |
| DEC-treated/FeLV-exposed | 6 | 0 | $10^1$ | $10^4$ | 2 |
| | | | $10^2$ | $10^3$ | 1 |
| | | | $10^2$ | $10^4$ | 1 |
| | | | $10^3$ | $10^2$ | 1 |
| | | | $10^4$ | $10^3$ | 1 |
| DEC-treated SPF/FeLV-naive | 2 | 0 | <$10^1$ | <$10^1$ | 2 |
| Untreated SPF/FeLV-naive | 4 | 0 | <$10^1$ | <$10^1$ | 4 |
| Total cats | 39 | | | | |

TABLE 2

Effect of DEC treatment[a] of cats after 1 cc i.m. Leukocell FeLV vaccine

| Status of cats prior to vaccination | No. cats studied | Procedure | Serum antibody to FOCMA[b] | | |
|---|---|---|---|---|---|
| | | | pre vaccine | 6 wks post vaccine | 10 wks post vaccine |
| FeLV-naive | 2 | vaccinated/treated | <1:$10^1$ | 1:$10^3$ | 1:$10^1$ |
| | | | <1:$10^1$ | 1:$10^3$ | 1:$10^1$ |
| FeLV-exposed | 1 | vaccinated/treated | 1:$10^1$ | 1:$10^4$ | 1:$10^4$ |
| FeLV-naive | 2 | vaccinated | <1:$10^1$ | 1:$10^2$ | <1:$10^1$ |
| | | | <1:$10^1$ | 1:$10^3$ | <1:$10^1$ |
| FeLV-exposed | 1 | vaccinated | 1:$10^1$ | 1:$10^3$ | 1:$10^2$ |

[a]DEC was given 10 mg/kg/day orally as a single dose per day for 2 weeks following vaccination.
[b]Testing for antibody to FOCMA was performed using IMI on FL-74 cells at tenfold dilutions of serum from 1:$10^1$ to 1:$10^5$ in PBS.

TABLE 3

Effect of DEC on titers of serum antibody to feline infectious peritonitis in domestic cats as determined by indirect membrane immunofluorescence[a]

| | Untreated | | DEC-treated | |
|---|---|---|---|---|
| Time Cat group | 0 serum antibody | 8 weeks/ Effect serum antibody | 0 serum antibody | 8 weeks/ Effect serum antibody |
| FeLV naive/FeLV-vaccinated[b] (FeLV leutocyte antigen negative) | 8192 2048 | 8192/NC 2048/NC | 256 1024 | 512/2-fold inc 4096/4-fold inc |
| FeLV-exposed/FeLV-vaccinated[c] (FeLV leukocyte antigen negative) | 4096 | 8192/2-fold inc | 512 | 512/NC |
| FeLV-infected offspring of | 512 | 2048/4-fold inc | 128 | 2048/16-fold inc |

TABLE 3-continued

Effect of DEC on titers of serum antibody to feline infectious peritonitis in domestic cats as determined by indirect membrane immunofluorescence[a]

| Time Cat group | Untreated | | DEC-treated | |
|---|---|---|---|---|
| | 0 serum antibody | 8 weeks/ Effect | 0 serum antibody | 8 weeks/ Effect |
| FeLV queen[d] (FeLV leukocyte antigen positive) | 512 | 2048/4-fold inc | 256 | 512/ 2-fold inc |
| FeLV Rickard-inoculated cats[e] (FeLV leukocyte antigen positive)[f] | 8192 | 16384/2-fold inc | 16834 | 8192/2-fold dec |
| | 4096 | 2048/2-fold dec | 4096 | 16384/4-fold inc |

NC, no change; inc, increase; dec, decrease;
[a]performed under code by Tufts Diagnostic Veterinary Laboratory, Jamaica Plain, MA; result given is reciprocal of highest dilution scored positive;
[b]4 FeLV-naive cats from a specific pathogen free breeding colony; 2 treated with DEC 10 mg/kg/day p.o. for 2 weeks after 1 dose of 1 cc LEUKOCELL FeLV vaccine i.m., 2 untreated;
[c]outbred cats with known epidemiologic exposure to FeLV; 1 treated with DEC 10 mg/kg/day p.o. for 2 weeks after 1 dose of 1 cc LEUKOCELL i.m.; 1 untreated;
[d]littermates first positive for FeLV leukocyte antigen at age 2 months; 2 treated with DEC 10 mg/kg/day p.o. on a continuous basis; 2 untreated;
[e]littermates inoculated with the Rickard strain of FeLV in the post-weaning period; 2 were treated with DEC 10 mg/kg/day p.o. for 1 month at 9 months of age; 2 untreated;
[f]FeLV viral antigen in peripheral blood leukocytes was tested at the Laboratory of Veterinary Oncology, Memorial Sloan-Kettering Cancer Center, New York City.

TABLE 4

Effect of DEC on testing serum samples for antibody to HIV-1 by EIA: relationship to clinical status

| No. tested/ clinical status | No. pos. by RIP-SDS/PAGE | No. pos. by EIA | No. pos. by EIA + DEC | Significant effect of DEC on absorbance values of EIA? |
|---|---|---|---|---|
| 75/ asymptomatic | 0 | 17 | 15 | no |
| 25/ asymptomatic | 25 | 25 | 25 | no |
| 15/ asymptomatic | 15 | 15 | 15 | not analyzed |
| 7/ AIDS-related disease | 7 | 7 | 7 | not analyzed |
| 18/ AIDS-related disease | 18 | 18 | 18 | yes; p < .0007 |

TABLE 5

Effect of DEC on testing serum samples for antibody to HIV-1 by EIA: relationship to HIV-1 antibody profile

| No. tested/ HIV-1 antibody profile | No. pos. by RIP-SDS/ PAGE | No. pos. by EIA | No. pos. by EIA | Significant effect of DEC on absorbance values of EIA? |
|---|---|---|---|---|
| 18/testing positive for antibody to gp 120/160 and p24 | 18 | 18 | 18 | no |
| 25/testing positive for antibody to gp120/160 but negative for antibody to p24 | 25 | 25 | 25 | yes; p < .03 |

TABLE 6

Effect of DEC on testing serum samples for antibody to HIV-1 by EIA: relationship to the number of helper T lymphocytes/mm$^3$ blood

| No. tested/ helper T-lymphocyte status | No. positive by EIA | No. positive by EIA + DEC | Significant effect of DEC on absorbance values of EIA? |
|---|---|---|---|
| 29/helper T-lymphocyte counts >500/mm$^3$ | 29 | 29 | no |
| 14/ helper T-lymphocytes <500/mm$^3$ | 14 | 14 | yes; p < .03 |

What is claimed is:

1. A method for treatment of viral infection which comprises administering to a host in need of such treatment an effective amount of diethylcarbamazine, or its therapeutically useful homologs, or pharmaceutically acceptable salts.

2. The method of claim 1 wherein the infection is caused by a retrovirus.

3. The method of claim 2 wherein the virus is human immunodeficiency virus (HIV) or feline leukemia virus (FeLV)

4. The method of claim 3 wherein the virus is HIV.

5. The method of claim 1 wherein the amount administered is about 0.5–20 mg/kg of body weight.

6. A method for immunomodulation of a host harboring a pathogen or neoplasia which comprises administering to said host an immunomodulating effective amount of diethylcarbamazine, or its therapeutically useful homologs, or pharmaceutically acceptable salts.

7. The method of claim 6 wherein the host harbors a virus or a neoplasia.

8. The method of claim 7 wherein the virus is a retrovirus.

9. The method of claim 8 wherein the virus is HIV or FeLV.

10. The method of claim 9 wherein the virus is HIV.

11. The method of claim 6 wherein the amount administered is about 0.5–20 mg/kg of body weight.

12. A method of prevention of viral infection which comprises administering to a host an anti-viral effective amount of diethylcarbamazine, or its therapeutically useful homologues, or pharmaceutically acceptable salts.

13. The method of claim 12 wherein the virus is a retrovirus.

14. The method of claim 13 wherein the virus is HIV or FeLV.

15. The method of claim 14 wherein the virus is HIV.

16. The method of claim 14 wherein the amount is about 0.5–20 mg/kg of body weight.

17. In a method for prevention of pathogenic infection which comprises administering to a host an immunogenic-effective amount of a composition comprising at least one antigen of said pathogen, the improvement comprising administering with said antigen an effective amount of diethylcarbamazine, or its therapeutically useful homologous, or a pharmaceutically acceptable salt as adjuvant.

18. The method of claim 17 wherein the pathogen is a virus.

19. The method of claim 18 wherein the pathogen is a retrovirus.

20. The method of claim 19 wherein the virus is HIV or FeLV.

21. The method of claim 20 wherein the virus is HIV.

22. The method of claim 17 wherein the adjuvant is added to the composition comprising the antigen.

23. The method of claim 12 wherein the amount of adjuvant is about 0.05-2 mg/cc of composition.

24. The method of claim 17 wherein the adjuvant is administered separately from the composition comprising the antigen.

25. The method of claim 24 wherein the amount of adjuvant is about 0.5-20 mg/kg of body weight.

26. In an immunoassay for detection of antibody in a fluid sample comprising contacting said sample with an antigen capable of reacting with said antibody, the improvement comprising adding to said fluid sample, prior to contact with the antigen, a reaction-enhancing effective amount of diethylcarbamazine or a homologue, or pharmaceutically acceptable salt thereof.

27. The immunoassay of claim 26 wherein the amount is about 0.005-5 mg/ml of fluid sample.

28. In an immunodiagnostic method for detection of a pathogen-associated antibody comprising contacting a serum sample of an individual suspected of harboring said pathogen with a pathogen specific antigen, the improvement comprising administering to said individual an effective amount of diethylcarbamazine, or homologue, or pharmaceutically acceptable salt thereof, prior to collection of the serum sample.

29. The method of claim 28 wherein the pathogen is a virus.

30. The method of claim 29 wherein the virus is a retrovirus.

31. The method of claim 30 wherein the virus is HIV or FeLV.

32. The method of claim 31 wherein the virus is HIV.

33. The method of claim 31 wherein the amoung is about 0.5-20 mg/kg of body weight.

34. A composition for the prevention of viral infection which comprises an immunogenic effective amount of at least one viral antigen in combination with an adjuvant-effective amount of diethylcarbamazine, or homologue, or pharmaceutically acceptable salt thereof.

35. The composition of claim 34 wherein the virus is a retrovirus.

36. The composition of claim 34 wherein the virus is HIV or FeLV.

37. A composition for treatment of viral infection comprising an effective amount of antiviral chemotherapeutic agent in combination with an effective amount of diethylcarbamazine, or a homologue, or pharmaceutically acceptable salt thereof.

38. The composition of claim 37 wherein the virus is a retrovirus.

39. The composition of claim 38 wherein the virus is HIV or FeLV.

40. The composition of claim 39 wherein the chemotherapeutic agent is AZT, fusidic acid, Ampligen, interferon, interleukin-2, IMREG-1, or dideoxycytidine.

* * * * *

UNITED STATES PATENT AND TRADEMARK OFFICE
CERTIFICATE OF CORRECTION

PATENT NO. : 4,900,548

DATED : February 13, 1990

INVENTOR(S) : Lynn W. Kitchen

It is certified that error appears in the above-indentified patent and that said Letters Patent is hereby corrected as shown below:

Column 1, after line 10, insert the following:

"This invention was made with government support under NIH Grant No. HL 33774, awarded by the National Institute of Health. The government has certain rithts in the invention."

Signed and Sealed this

Twelfth Day of April, 1994

Attest:

BRUCE LEHMAN

Attesting Officer

Commissioner of Patents and Trademarks